(12) United States Patent
Olsen

(10) Patent No.: US 6,277,633 B1
(45) Date of Patent: Aug. 21, 2001

(54) LENTIVIRUS-BASED GENE TRANSFER VECTORS

(75) Inventor: John C. Olsen, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/076,707

(22) Filed: May 12, 1998

Related U.S. Application Data

(60) Provisional application No. 60/046,891, filed on May 13, 1997.

(51) Int. Cl.[7] .......... C12N 15/09; C12N 15/687; C12N 15/86; A61K 48/00; A01N 63/00
(52) U.S. Cl. .......... 435/320.1; 435/456; 435/457; 536/23.1; 424/93.21; 514/44
(58) Field of Search .......... 424/93.1, 93.21; 435/5, 6, 7.21, 455, 456, 465, 466, 362, 375, 320.1, 457; 536/23.5, 23.72, 24.1, 23.1; 514/44

(56) References Cited

U.S. PATENT DOCUMENTS

| | | | |
|---|---|---|---|
| 4,650,764 | 3/1987 | Temin et al. | 435/350 |
| 5,091,309 | 2/1992 | Schlesinger et al. | 435/69.1 |
| 5,240,846 | 8/1993 | Collins et al. | 435/371 |
| 5,501,979 | 3/1996 | Geller et al. | 435/320.1 |
| 5,576,206 | 11/1996 | Schlegel | 435/371 |
| 5,817,491 | 10/1998 | Yee et al. | 435/456 |
| 6,013,516 | 1/2000 | Verma et al. | 435/325 |

FOREIGN PATENT DOCUMENTS

| | | |
|---|---|---|
| 0 453 242 A1 | 4/1991 | (EP) . |
| WO/95/14091 | 5/1995 | (WO) . |
| WO/95/27044 | 10/1995 | (WO) . |
| WO/95/31565 | 11/1995 | (WO) . |
| WO/96/27672 | 9/1996 | (WO) . |
| WO/96/35454 | 11/1996 | (WO) . |
| WO/96/35777 | 11/1996 | (WO) . |
| WO/96/35798 | 11/1996 | (WO) . |
| WO/96/36364 | 11/1996 | (WO) . |
| WO/97/12622 | 4/1997 | (WO) . |
| WO/98/17815 | 4/1998 | (WO) . |
| WO/98/17816 | 4/1998 | (WO) . |

OTHER PUBLICATIONS

Richardson, Jennifer, H., "Helper virus–free transfer of human immunodeficiency virus type 1 vectors", Journal of General Virology, vol. 76, pp. 691–696, 1995.*

Cohen; "New role for HIV: A Vehicle For Moving Genes Into Cells"; *Science*, vol. 272:195 (1996).

Friedmann; "Progress Toward Human Gene Therapy"; *Science*, vol. 244:1275–81 (1989).

Hart, et al.; "Reduced Retroviral Entry Into Polarized Airway Epithelia"; 1996 Cystic Fibrosis Conference, Abstract No. 246.

(List continued on next page.)

*Primary Examiner*—David Guzo
*Assistant Examiner*—Gerald G. Leffers, Jr.
(74) *Attorney, Agent, or Firm*—Myers Bigel Sibley & Sajovec

(57) ABSTRACT

A recombinant lentiviral vector expression system comprises a first vector that comprises a nucleic acid sequence of at least part of the Equine Infectious Anemia Virus (EIAV) genome. The vector contains at least one defect in at least one gene encoding an EIAV structural protein, but is preferably a gag|pol expression vector. The expression system further comprises a second vector, also comprising a nucleic acid sequence of at least part of the Equine Infectious Anemia Virus (EIAV) genome, and additionally containing a multiple cloning site wherein a heterologous gene may be inserted. The expression system also comprises a third vector which expresses a viral envelope protein. The first and third vectors are packaging signal-defective. When the expression system is transfected into a lentivirus-permissive cell, replication-defective EIAV particles may be produced, which particles are useful in delivering heterologous genes to a broad range of both dividing and non-dividing cells.

29 Claims, 8 Drawing Sheets

OTHER PUBLICATIONS

Johnson, et al.; In Vivo Airway Gene Transfer and In Vitro Correction of CF Airway Cells Without Selection By a VSV–G Pseudotyped Retroviral Vector, 1996 Cystic Fibrosis Conference, Abstract No. 247.

Landau, et al; "Packaging System for Rapid Production of Murine Leukemia Virus Vectors with Variable Tropism"; *Virology*, vol. 66, No. 8:5110–13 (1992).

Naldini, et al.; "In Vivo Gene Delivery and STable Transduction of Nondividing Cells by a Lentiviral Vector"; *Science*, vol. 272:263–67 (1996).

Pear, et al.; "Production of high–titer helper–free retroviruses by transient transfection"; *Proc. Natl. Acad. Science*, vol. 90:8392–96 (1993).

Perry, et al.; "The Surface Envelope Protein Gene Region of Equine Infectious Anemia Virus Is Not an Important Determinant of Tropism In Vitro"; *Virology*, vol. 66, No. 7:4085–97 (1992).

Tan, et al.; "Inhibitory Activity of the Equine Infectious Anemia Virus Major 5' Splice Site in the Absence of Rev"; *Virology*, vol. 70, No. 6:3645–58 (1996).

Ory et al.; A stable human–derived packaging cell line for production of high titer retrovirus/vesicular stomatitis virus G pseudotypes, *Proc. Natl. Acad. Sci. USA*, 93:11400–11406 (1996).

Robin A. Weiss; Retrovirus classification and cell interactions, *Journal of Antimicrobial Chemotherapy*, 37:1–11 (1996).

Maury et al.; Cellular and Viral Specificity of Equine Infectious Anemia Virus Tat Transactivation, *Virology*, 200:632–642 (1994).

Zufferey et al.; Multiply attenuated lentiviral vector achieves efficient gene delivery in vivo, *Nature Biotechnology*, 15:871–875 (1997).

\* cited by examiner

LENTIVIRUS-BASED GENE TRANSFER VECTORS

RELATED APPLICATIONS

This application claims the benefit of U.S. Provisional Application Ser. No. 60/046,891, filed May 13, 1997, which application is incorporated herein in its entirety.

FIELD OF THE INVENTION

This invention relates to viruses as vectors useful in gene delivery, and more specifically to lentiviral vectors useful in gene delivery to non-dividing and dividing cells.

BACKGROUND OF THE INVENTION

The capacities to introduce a particular foreign or native gene sequence into a mammalian cell and to control the expression of that gene are of substantial value in the fields of medical and biological research. Such capacities provide a means for studying gene regulation, and for designing a therapeutic basis for the treatment of disease.

The introduction of a particular foreign or native gene into a mammalian host cell is facilitated by introducing a gene sequence into a suitable nucleic acid vector. A variety of methods have been developed which are capable of permitting the introduction of such a recombinant vector into a desired host cell. In contrast to methods which involve DNA transformation or transfection, the use of viral vectors can result in the rapid introduction of the recombinant molecule in a wide variety of host cells. In particular, viral vectors have been employ ed in order to increase the efficiency of introducing a recombinant nucleic acid vector into host cells. Viruses that have been employed as vectors for the transduction and expression of exogenous genes in mammalian cells include SV40 virus (see, e.g., H. Okayama et al., *Molec. Cell Biol.* 5, 1136–1142 (1985)); bovine papilloma virus (see, e.g., D. DiMalo et al., *Proc. Natl. Acad. Sci. USA* 79, 4030–4034 (1982)); adenovirus (see, e.g., J. E. Morin et al., *Proc. Natl. Acad. Sci. USA* 84, 4626 (1987)), adeno-associated virus (AAV; see, e.g., N. Muzyczka et al., *J Clin. Inveit.* 94, 1351 (1994)); herpes simplex virus (see, e.g., A. I. Geller, et al., *Science* 241, 1667 (1988)), and others.

Retrovirus-based vectors are particularly favored as tools to achieve stable, integrated gene transfer of foreign genes into mammalian cells. Retroviruses that have been employed as vectors for the introduction and expression of exogenous genes in mammalian cells include the Moloney murine sarcoma virus (T. Curran et al., *J. ViroL.* 44, 674–682 (1982); A. Gazit et al, *J Virol.* 60, 19–28 (1986)) and murine leukemia viruses (MuLV; A. D. Miller, *Curr. Tsp. Microbiol. Immunol.* 158, 1–24 (1992).

Efforts to introduce recombinant molecules into mammalian cells have been hampered by the inability of many cells to be infected by the above-described viral or retroviral vectors. Limitations on retroviral vectors, for example, include a relatively restricted host range, based in part on the level of expression of the membrane protein that serves as the viral receptor. M. P. Kavanaugh et al., *Proc. Natl. Acad. Sci USA* 91, 7071–7075 (1994). Other limitations include the inability to integrate into non-dividing cells (e.g., neurons, hepatocytes, myofibers, hematopoictic stem cells), modest vector titers available with current packaging systems, and the fragility of vector particles that precludes purification and concentration.

Lentiviruses are a subgroup of retroviruses that are capable of infecting non-dividing cells. L. Naldini et al. report a lentiviral vector system based on the human immunodeficiency virus (HIV) that is capable of transducing heterologous gene sequences into non-proliferative HeLa cells and rat fibroblasts, as well as into human primary macrophages and terminally differentiated neurons. *Science* 272, 263–267 (1996). However, the use of such a system in humans raises serious safety concerns, due to the possibility of recombination by the vector into a virulent and disease-causing form.

Accordingly, a need remains for a safe and efficient lentiviral vector systems capable of mediating gene transfer into a broad range of dividing and non-dividing cells.

SUMMARY OF THE INVENTION

The present invention is directed to the transfer ,of heterologous gene sequences into cells using Equine Infectious Anemia Virus (EIAV)-derived vectors for gene delivery.

A first aspect of the present invention is a recombinant lentiviral vector expression system including a first vector comprising a nucleic acid sequence of at least part of the Equine Infectious Anemia Virus (EIAV) genome, wherein the vector (i) contains at least one defect in at least one gene encoding an EIAV structural protein, and (ii) contains a defective packaging signal. The expression system additionally includes a second vector comprising a nucleic acid sequence of at least part of the EIAV genome, wherein the vector (i) contains a competent packaging signal, and (ii) contains a multiple cloning site wherein a heterologous gene may be inserted. The vector expression system also includes a third vector comprising a nucleic acid sequence of a virus, wherein the third vector (i) expresses a viral envelope protein, and (ii) contains a defective packaging signal.

A second aspect of the present invention is a method of producing a replication-defective lentivirus particle, comprising transfecting a cell with a vector expression system of the invention as described above.

A third aspect of the present invention is a method of delivering a heterologous gene to a target cell, comprising transfecting said target cell with a vector expression system of the invention as described above.

A fourth aspect of the present invention is a method of producing a lentiviral stock comprising (a) transfecting a producer cell with a vector expression system of the invention as described above; (b) growing the producer cell under cell culture conditions sufficient to allow production of replication-defective lentivirus particles in the cell; and (c) collecting the replication-defective lentivirus particles from the producer cell.

The foregoing and other aspects of the invention are explained in detail in the drawings herein and the specification set forth below.

BRIEF DESCRIPTION OF THE DRAWINGS

In FIG. 8, open circles represent concentrated virus particles, while closed circles represent unconcentrated virus particles. Dosage of the EC-lacZ vector is represented on the x-axis in units of $\mu$L virus/mL inoculum, while infectivity is represented on the y-axis as percentage of cells positive for X-gal.

DETAILED DESCRIPTION OF THE INVENTION

Figure 1:
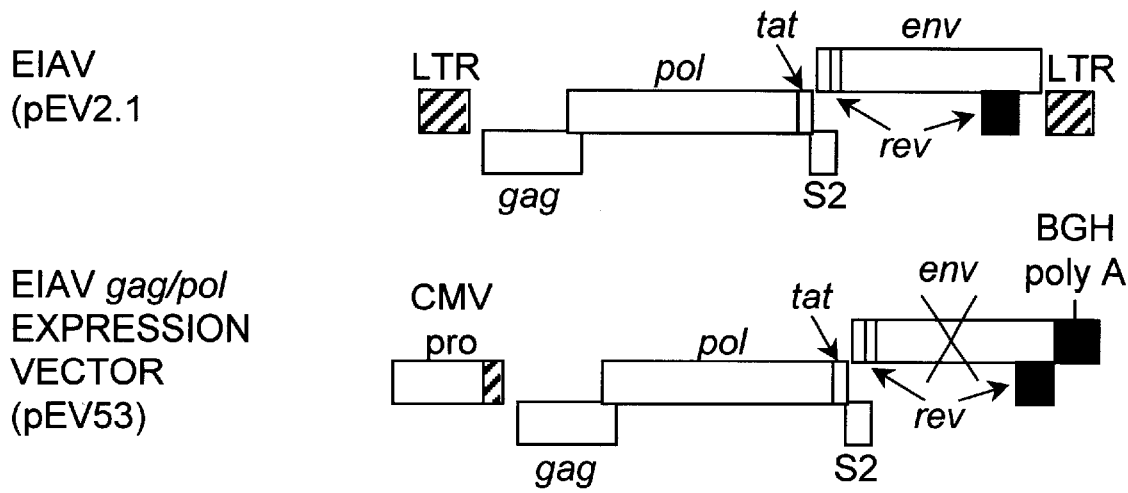
FIG. 1 is a schematic illustration of plasmid constructs used to generate EIAV-derived vectors of the present invention. Only a portion of each plasmid is depicted.
Figure 1:
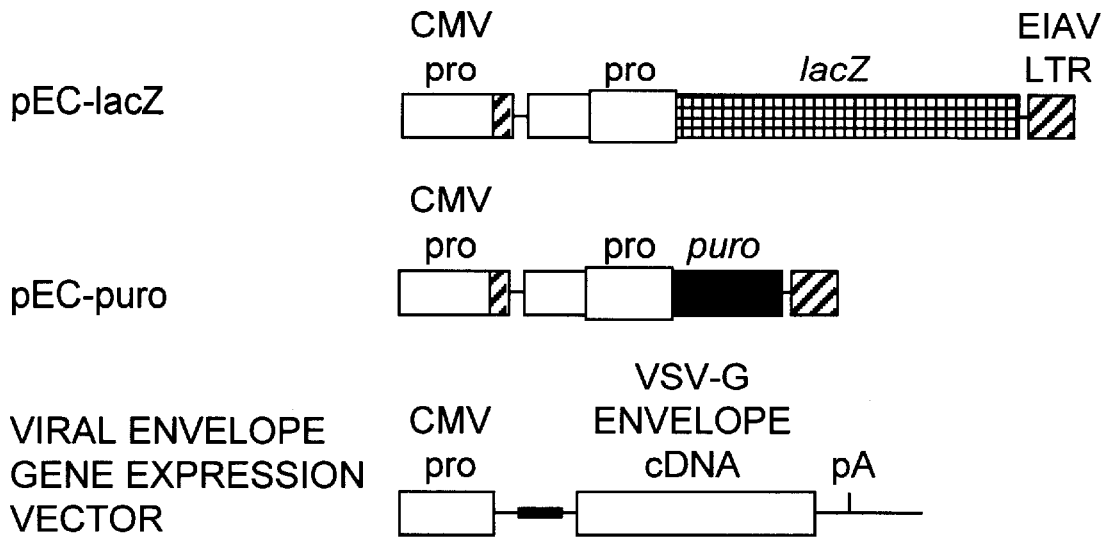

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will fully convey the scope of the invention to those skilled in the art.

I. The Equine Infectious Anemia Virus Genome

The Equine Infectious Anemia Virus (EIAV) is a member of the lentivirus genus of the retrovirus family. The wild type EIAV virus has a dimeric RNA genome (single-stranded, positive polarity) that is packaged into a spherical enveloped virion containing a nucleoprotein core. Replication of the wild type EIAV genome occurs via reverse transcription and integration into the host cell genome. The genome contains three genes that encode the structural proteins gag, pol, and env, and long terminal repeats (LTR) at each end of the integrated viral genome. In addition to the gag, pol, and env sequence,; common to all retroviruses, the EIAV genome contains several short open reading frames (ORFs). These short ORFs are translated from multiply spliced mRNAs. ORF S1 encodes the transcriptional transactivator tat. ORF S2 encodes a protein whose function is unknown, and the ORF S3 appears to encode a rev protein. It is thought that rev is required for the efficient expression of gag, pot and env. Rev acts post-transcriptionally by interacting with an RNA sequence known as the rev-responsive element (RRE), which is located in EIAV within the env gene.

The wild type genome of EIAV also contains several cis-acting sequences, including the R sequence (short repeat at each end of the genome); the U5 sequence (unique sequence element immediately after the R sequence); the U3 sequence (unique sequence element located downstream from the structural proteins); promoter elements that control transcriptional initiation of the integrated provirus; a packaging sequence (herein referred to interchangeably as a packaging site or a packaging signal); and a 5'-splice donor site.

II. EIAV Vectors of the Present Invention

The vectors of the present invention provide a means for replicating and expressing heterologous nucleic acid independent of the host cell nucleus in a broad phylogenetic range of host cells. This vector-mediated incorporation of heterologous nucleic acid into a host cell is referred to as transfection or infection of the host cell, wherein infection means the use of virus particles, and transfection means the use of naked molecules of nucleic acid.

The vectors of the present invention additionally permit the incorporation of heterologous nucleic acid into virus particles, thereby providing a means for amplifying the number of infected host cells containing heterologous nucleic acid therein. The incorporation of the heterologous nucleic acid facilitates the replication of the heterologous nucleic acid within the viral particle, and the subsequent production of a heterologous protein therein. A heterologous protein is herein defined as a protein or fragment thereof wherein all or a portion of the protein is not expressed by the host cell. A nucleic acid or gene sequence is said to be heterologous if it is not naturally present in the wild type of the viral vector used to deliver the gene into a cell (e.g., the wild-type EIAV genome). The term nucleic acid sequence or gene sequence, as used herein, is intended to refer to a nucleic acid molecule (preferably DNA). Such gene sequences may be derived from a variety of sources including DNA, cDNA, synthetic DNA, RNA or combinations thereof. Such gene sequences may comprise genomic DNA which may or may not include naturally occurring introns. Moreover, such genomic DNA may be obtained in association with promoter sequences or poly-adenylation sequences. The gene sequences of the present invention are preferably cDNA. Genomic or CDNA may be obtained in any number of ways. Genomic DNA can be extracted and purified from suitable cells by means well-known in the art. Alternatively, mRNA can be isolated from a cell and used to prepare cDNA by reverse transcription, or other means.

It is an object of this invention to generate vectors capable of carrying out one single round of replication in the process of delivering a gene of interest to a target cell. An aspect of this technology is a gene delivery system that excludes the transfer of viral genes to the target cell. This is accomplished by physically separating expression vectors encoding viral genes from the vector encoding the gene of interest. The separate expression vectors are transfected into a permissive cell (e.g., a "producing cell"). Viral gene products are necessary for the production of virus particles. However, in the present invention, genes coding for these genes are located on expression vectors that contain defective packaging signals; accordingly, the genes that code for the structural proteins are not packaged.

The phrases "structural protein" or "EIAV structural protein" as used herein refer to the encoded proteins which are required for encapsidation (e.g., packaging) of the EIAV genome, and include gag, pol and env.

The term "defective" as used herein refers to a nucleic acid sequence that is not functional with regard to either encoding its gene product or serving as a signaling sequence. To illustrate, a defective env gene sequence will not encode the env protein; a defective packaging signal will not facilitate the packaging of the nucleic acid molecule the defective signal is located on. Nucleic acid sequences may be made defective by any means known in the art, including by the deletion of some or all of the sequence, by placing the sequence out-of-frame, or by otherwise blocking the sequence.

As used herein, the terms "deleted" or "deletion" mean either total deletion of the specified segment or the deletion of a sufficient portion of the specified segment to render the segment inoperative or nonfunctional, in accordance with standard usage. The term "replication defective" as used herein, means that the vectors that encode EIAV structural proteins cannot be encapsidated in the target cell after transfection of the vectors. The resulting lentivirus particles are replication defective inasmuch as the packaged vector does not include all of the viral structural proteins required for encapsidation, at least one of the required structural proteins being deleted therefrom, such that the packaged vector is not capable of replicating the entire viral genome.

The preferred vectors of the present invention are derived from EIAV. Native EIAV nucleic acid may be isolated from cells infected with the virus, and vectors prepared therefrom. An exemplary method for preparing EIAV vectors is provided in S. T. Perry, et al., *J. Virol.* 66, 4085–4097 (1992). For example, cDNA may be produced from EIAV RNA by reverse transcriptase, using methods known in the art. Double-stranded EIAV cDNA may then be produced and cloned into a cloning vector, such as a bacterial cloning vector. Any cloning vector, such as bacterial, yeast or eukaryotic vectors, known and used by those skilled in the art, may be used. The vectors of the present invention preferably comprise cDNA complementary to at least part of the RNA genome of EIAV. One vector may contain an heterologous CDNA molecule, which molecule can be introduced into human or animal cells to achieve transcription or expression of the heterologous molecule. The cDNA molecules will comprise cDNA complementary to at least part of a EIAV genome and comprising part of RNA genome required for replication of the genome, with the cDNA molecule being placed under transcriptional control of a promoter sequence functional in the cell.

A promoter sequence of the present invention may comprise a promoter of eukaryotic or prokaryotic origin, and will be sufficient to direct the transcription of a distally located sequence (i.e. a sequence linked to the 5' end of the promoter sequence) in a cell. The promoter region may also include control elements for the enhancement or repression of transcription. Suitable promoters are the cytomegalovirus immediate early promoter (pCMV), the Rous Sarcoma virus long terminal repeat promoter (pRSV), and the SP6, T3, or T7 promoters. Enhancer sequences upstream from the promoter or terminator sequences downstream of the coding region may be optionally be included in the vectors of the present invention to facilitate expression. Vectors of the present invention may also contain additional nucleic acid sequences, such as a polyadenylation sequence, a localization sequence, or a signal sequence, sufficient to permit a cell to efficiently and effectively process the protein expressed by the nucleic acid of the vector. Exampled of preferred polyadenylation sequences are the SV40 early region polyadenylation site (C. V. Hall et al., *J Molec. App. Genet.* 2, 101 (1983)) and the SV40 late region polyadenylation site (S. Carswell and J. C. Alwine, *Mol. Cell Biol.* 9, 4248 (1989)). Such additional sequences are inserted into the vector such that they are operably linked with the promoter sequence, if transcription is desired, or additionally with the initiation and processing sequence if translation and processing are desired. Alternatively, the inserted sequences may be placed at any position in the vector. The term "operably linked" is used to describe a linkage between a gene sequence and a promoter or other regulatory or processing sequence such that the transcription of the gene sequence is directed by an operably linked promoter sequence, the translation of the gene sequence is directed by an operably linked translational regulatory sequence, and the post-translational processing of the gene sequence is directed by an operably linked processing sequence.

Standard techniques for the construction of the vectors of the present invention are well-known to those of ordinary skill in the art and can be found in such references as Sambrook et al., *Molecular Clonining: A Laboratory Manual 2nd Ed.* (Cold Spring Harbor, N.Y., 1989). A variety of strategies are available for ligating fragments of DNA, the choice of which depends on the nature of the termini of the DNA fragments and which choices can be readily made by the skilled artisan.

In one embodiment of the present invention, a recombinant lentiviral expression system comprises three vectors. The first vector comprises a nucleic acid sequence of at least part of the Equine Infectious Anemia Virus (EIAV) genome, wherein the vector (i) contains at least one defect in at least one gene encoding an EIAV structural protein, and (ii) contains a defective packaging signal. The second vector comprises a nucleic acid sequence of at least part of the EIAV genome, wherein the vector (i) contains a competent packaging signal, and (ii) contains a multiple cloning site wherein a heterologous gene may be inserted. The third vector comprises a nucleic acid sequence of a virus, wherein the vector (i) expresses a viral envelope protein, and (ii) contains a defective packaging signal.

In one embodiment of the invention, the first vector is a gag/pol expression vector. Gag/pol expression vectors express EIAV proteins required for assembly and release of viral particles from cells, and include the genes encoding proteins gag and pol. The first vector may also express genes encoding the accessory proteins rev and tat. The open reading frame S2, encoding a protein whose function is unknown, may additionally be included in the first vector. The first vector is constructed to contain mutations that exclude retroviral-mediated transfer of viral genes. Such mutations may be a deletion of sequences in the viral env gene, thus excluding the possibility of generating replication-competent EIAV, or may be deletions of certain cis-acting sequence elements at the 3' end of the genome required for viral reverse transcription and integration. Accordingly, even if viral genes from this construct are packaged into viral particles, they will not be replicated and replication-competent wild-type viruses will not be generated.

Figure 2A:
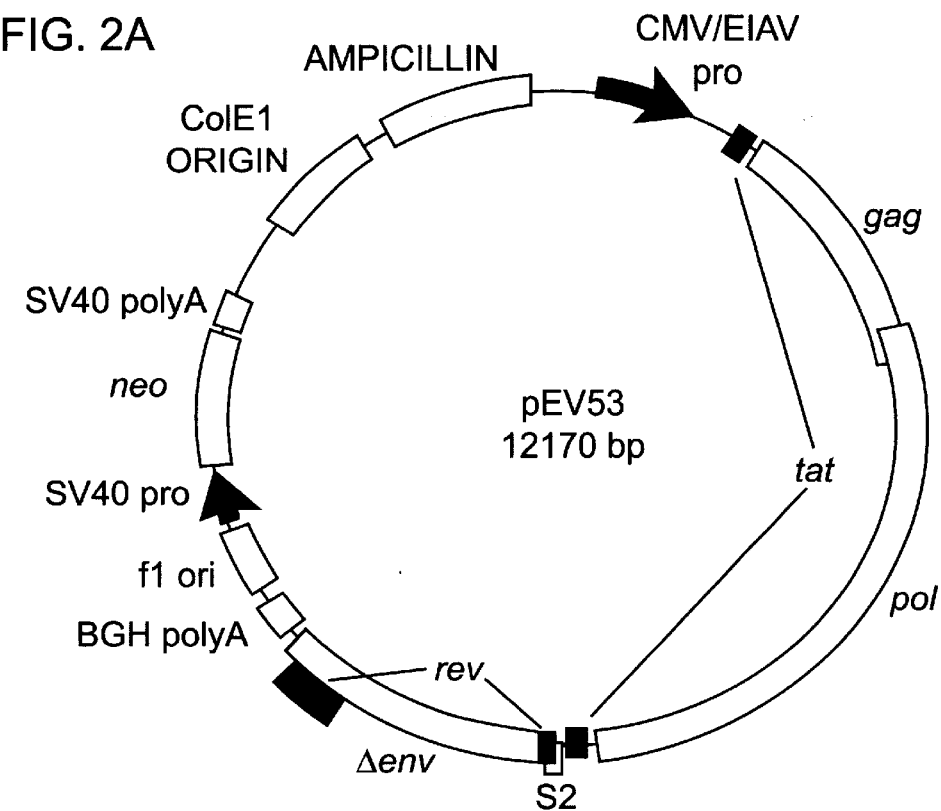
FIG. 2A is a schematic illustration of the plasmid pEV53.

In a preferred embodiment of the invention, the first vector of the expression system is the plasmid pEV53, shown in FIG. 2A. pEV53 is a 12170 base-pair (bp) plasmid and cDNA clone which at base pairs 209–1072 contains a chimeric CMV/EIAV enhancer promoter region located upstream from the EIAV tat coding regions (bp 1124–1210 and 5886–6026), the gag coding region (bp 1216–2676), the pol coding region (bp 2433–5874) and the ORF S2 7337 coding region (bp 6037–6234). The vector also contains a partial env coding region (bp 6063–7733) and rev coding regions (bp 6188–6288 and 7250–7654). The bovine growth hormone (BGH) polyadenylation signal is provided (bp 7759–7973), as is a phage f1 region (bp 8037–8450), an SV40 early promoter region and origin of replication (bp 8514–8839), a neomycin resistance coding region (bp 9685–9924), a ISV40 polyadenylation signal (bp 9685–9924), a Col E1 origin of replication (bp 10356–11029), and a β-lactamase (ampicillin resistance) coding region (bp 11174–12035).

Figure 2B:
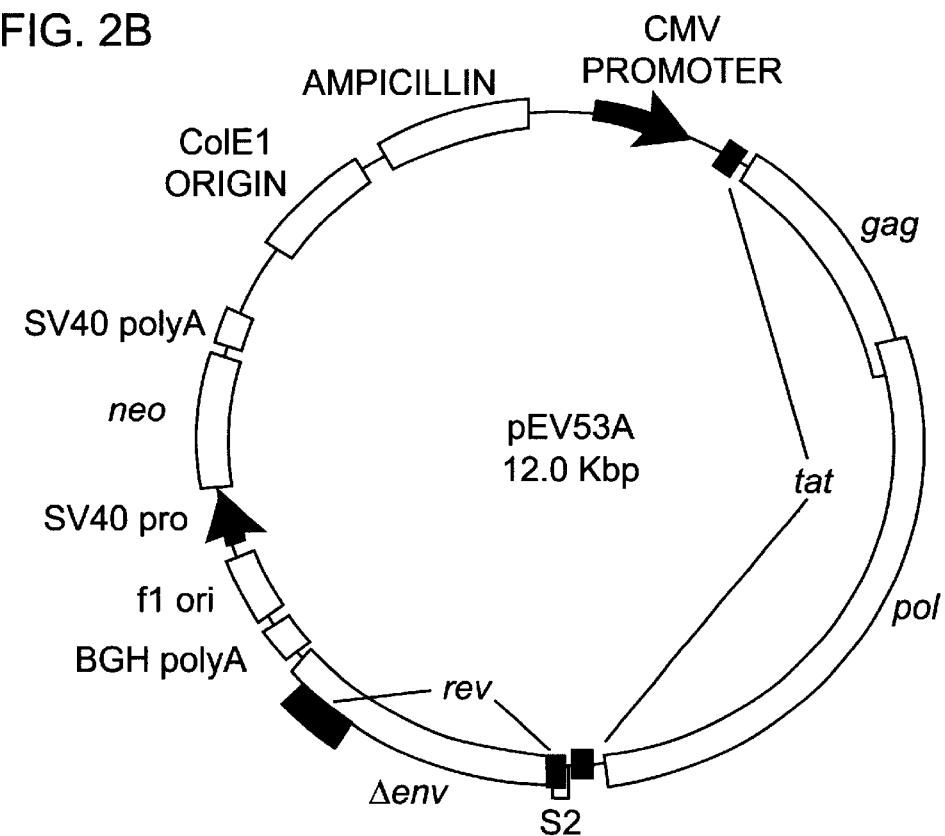
FIG. 2B is a schematic illustration of the plasmid pEV53A.

In a more preferred embodiment of the present invention, the first vector of the expression system is the plasmid pEV53A, shown in FIG. 2B. The plasmid pEV53A is derived from the pEV53 plasmid, wherein modifications have been made to further reduce the chances of retroviral-mediated transfer of viral genes without affecting the expression levels of EIAV proteins. In the plasmid pEV53A, all EIAV long terminal repeat (LTR) sequences containing promoter/enhancer elements and cis-acting sequence elements important for integration and the tRNA primer binding site sequence for initiation of reverse transcription has been deleted from pEV53. pEV53A is constructed from pEV53 by deleting nucleotides 902 through 1077 of pEV53.

The second vector of the expression system of the present invention is designed to serve as the vector for gene transfer, and contains all cis-acting sequence elements required to support reverse transcription (replication) of the vector genome, as well as a multiple cloning site for insertion of cDNA s encoding heterologous genes of interest. In the present invention, the vector encoding the gene of interest is a recombinant EIAV-derived vector that carries the genetic information to be transduced into a target cell, along with cis-acting sequence elements necessary for the packaging and integration of the viral genome. The second vector will preferably contain some portion of the gag coding sequence, as it is believed that certain parts of the gag sequence play a role in the packaging of the EIAV genome. Moreover, the 5' splice donor site contained in the LTR will preferably contain a mutation that increases the titer of the produced virus, as described in, e.g., W. Tan et al., *J. Virol.* 70, 3645–3658 (1996).

Figure 3:
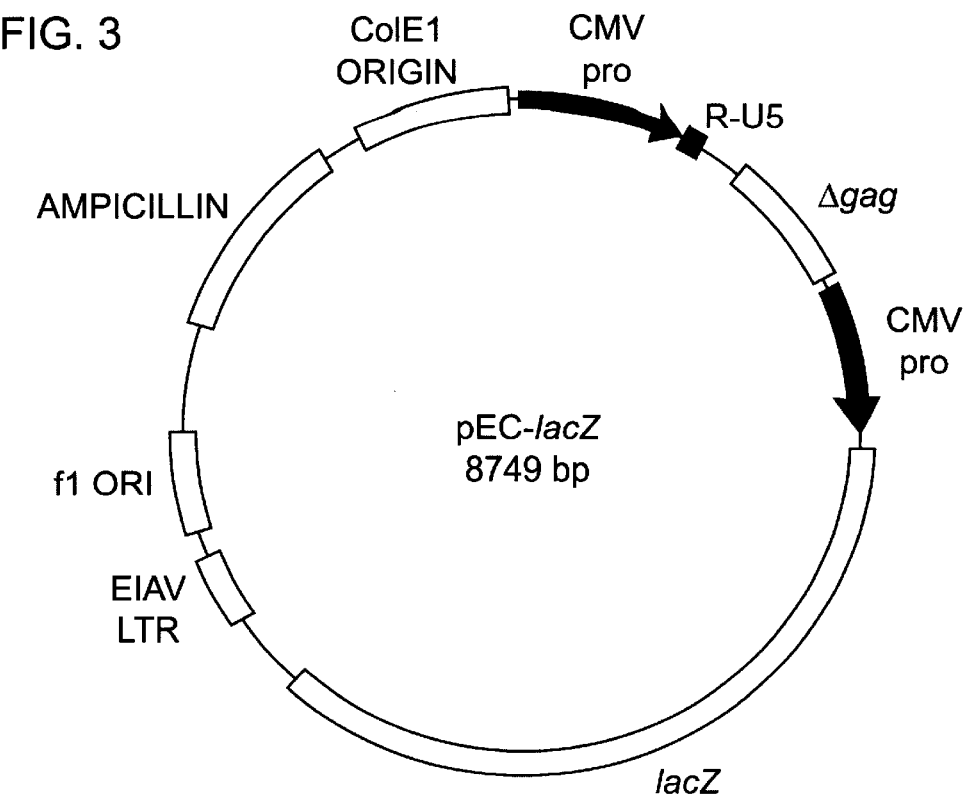
FIG. 3 is a schematic illustration of the plasmid pEC-lacZ.
Figure 4:
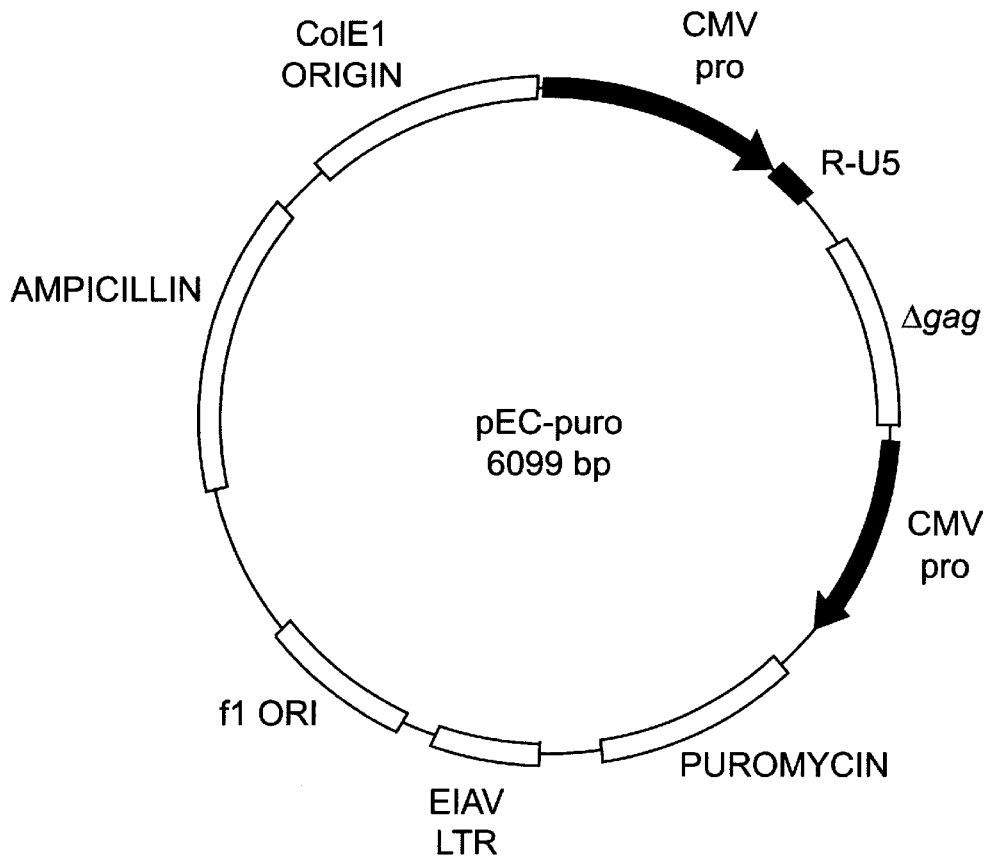
FIG. 4 is a schematic illustration of the plasmid pEC-puro.

Two examples of preferred second vectors are provided in FIGS. 3 and 4. FIG. 3 illustrates the plasmid and cDNA clone pEC-lacZ, a 8749 bp plasmid derived from EIAV that expresses the *E. Coli* lacZ reporter gene. The plasmid contains two CMV immediate-early enhancer promoter regions (located at bp 1–734 and 1609–2224), R-U5 sequence domains from the EIAV long terminal repeat (LTR) (bp 735–849), a partial EIAV gag sequence (bp 993–1570), the lacZ coding sequence (bp 2297–5437), a EIAV LTR sequence (bp 5752–6073), a phage f1 region (bp 6163–6618), an ampicillin resistance coding region (bp 7057–7917) and a ColE1 origin of replication (bp 8062–8736).

FIG. 4 illustrates the plasmid and cDNA clone pEC-puro, a 6099 bp plasmid derived from EIAV expressing the puromycin resistance gene. This vector also contains two CMV immediate-early enhancer promoter regions (bp 1–734 and 1609–2224), R-U5 sequence domains from the EIAV long terminal repeat (LTR) (bp 735–849), a partial gag sequence from EIAV (bp 993–1570), the puromycin resistance gene coding sequence (bp 2334–2933), an ELAV LTR sequence (bp 3102–3423), a phage f1 region (bp 3513–3968), an ampicillir, resistance coding region (bp 4407–5267) and a ColE 1 origin of DNA replication (bp 5412–6086).

As will be appreciated by one skilled in the art, the nucleotide sequence of the inserted heterologous gene sequence or sequences may be of any nucleotide sequence. For example, the inserted heterologous gene sequence may be a reporter gene sequence or a selectable marker gene sequence. A reporter gene sequence, as used herein, is any gene sequence which, when expressed, results in the production of a protein whose presence or activity can be monitored. Examples of suitable reporter genes include the gene for galactokinase, beta-galactosidase, chloramphenicol acetyltransferase, beta-lactamase, etc. Alternatively, the reporter gene sequence may be any gene sequence whose expression produces a gene product which affects cell physiology. Heterologous gene sequences of the present invention may comprise one or more gene sequences that already possess on ore more promoters, initiation sequences, or processing sequences.

A selectable marker gene sequence is any gene sequence capable of expressing a protein whose presence permits one to selectively propagate a cell which contains it. Examples of selectable marker genes include gene sequences capable of conferring host resistance to antibiotics (e.g., puromycin, ampicillin, tetracycline, kanamycin, and the like), or of conferring host resistance to amino acid analogues, or of permitting the growth of bacteria on additional carbon sources or under otherwise impermissible culture conditions. A gene sequence may be both a reporter gene and a selectable marker gene sequence. The most preferred reporter genes of the present invention are the lacZ gene which encodes the beta-galactosidase activity of *E. Coli*; and the gene encoding puromycin resistance.

Preferred reporter or selectable marker gene sequences are sufficient to permit the recognition or selection of the vector in normal cells. In one embodiment of the invention, the reporter gene sequence will encode an enzyme or other protein which is normally absent from mammalian cells, and whose presence can, therefore, definitively establish the presence of the vector in such a cell.

The heterologous gene sequence may also comprise the coding sequence of a desired product such as a suitable biologically active protein or polypeptide, immunogenic or antigenic protein or polypeptide, or a therapeutically active protein or polypeptide. Alternatively, the heterologous gene sequence may comprise a sequence complementary to an RNA sequence, such as an antisense RNA sequence, which antisense sequence can be administered to an individual to inhibit expression of a complementary polynucleotide in the cells of the individual.

Expression of the heterologous gene may provide immunogenic or antigenic protein or polypeptide to achieve an antibody response, which antibodies can be collected from an animal in a body fluid such as blood, serum or ascites.

In a preferred embodiment of the present invention, the third vector of the recombinant lentiviral expression system expresses a viral envelope protein. Such a vector will accordingly comprise a nucleic acid sequence encoding a viral protein under the control of a suitable promoter. It is possible to alter the host range of cells that the viral vectors of the present invention can infect by utilizing an envelope gene from another closely related virus. In other words, it is possible to expand the host range of the EIAV vectors of the present invention by taking advantage of the capacity of the envelope proteins of certain viruses to participate in the encapsidation of other viruses. In a particularly preferred embodiment of the present invention, the G-protein of vesicular-stomatitis virus (VSV-G; see, e.g., Rose and Gillione, *J. Virol.* 39, 519–528 (1981); Rose and Bergmann,

*Cell* 30, 753–762 (1982)), or a fragment or derivative thereof, is the envelope protein expressed by the third vector. VSV-G efficiently forms pseudotyped virions with genome and matrix components of other viruses. As used herein, the term "pseudotype" refers to a viral particle that contains nucleic acid of one virus but the envelope protein of another virus. In general, VSV-G pseudotyped vectors have a very broad host range, and may be pelleted to titers of high concentration by ultracentrifugation (e.g., according to the method of J. C. Burns, et al., *Proc. Natl. Acad. Sci. USA* 90, 8033–8037 (1993)), while still retaining high levels of infectivity.

Figure 5:
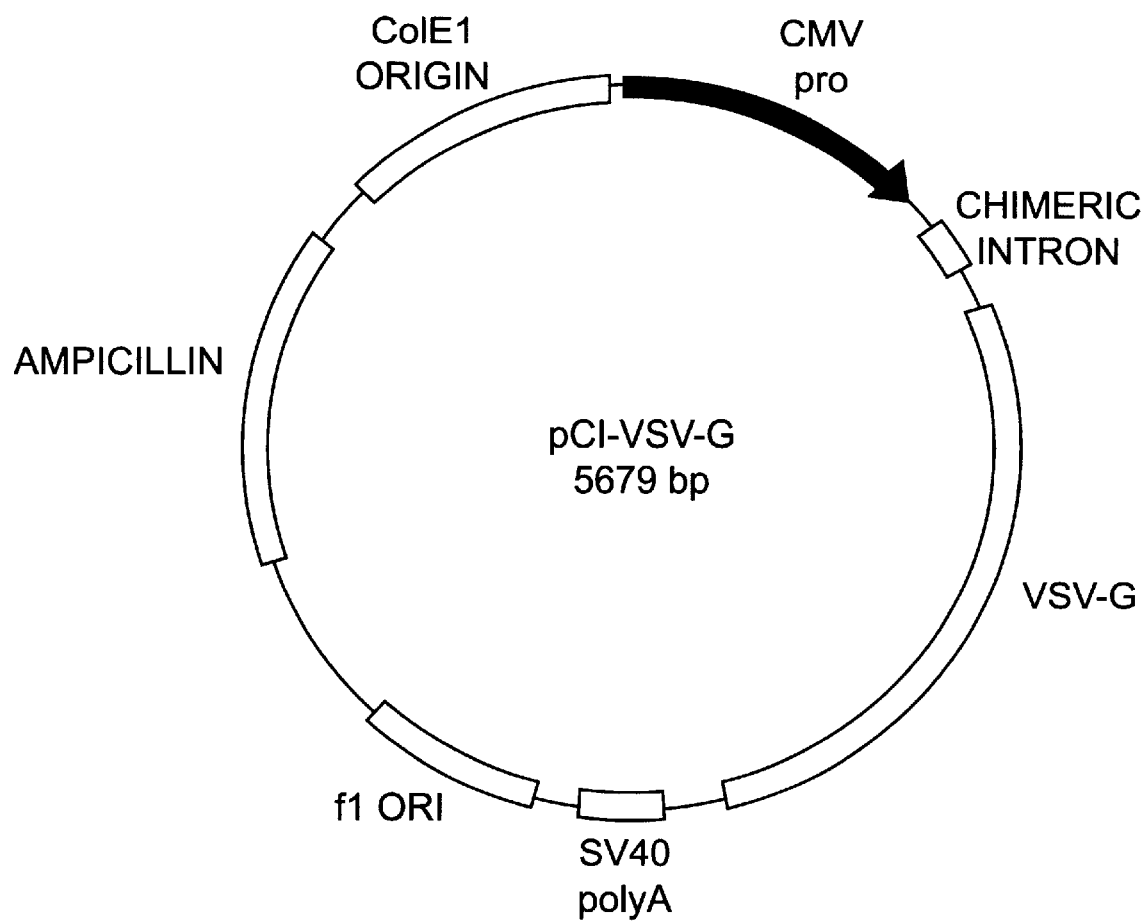
FIG. 5 is a schematic illustration of the plasmid pCI-VSV-G.

An illustrative and preferred example of a third vector of the present invention is shown in FIG. 5. This Figure illustrates the plasmid and CDNA clone pCI-VSV-G, a preferred expression vector for the envelope glycoprotein VSV-G. The plasmid contains 5679 base pairs and includes the CMV immediate-early enhancer promoter region (bp 1–795), a chimeric intron region (bp 857–989), the VSV-G coding region (bp 1088–2633), a phage f1 region (3093–3548), a SV40 late polyadenylation signal (bp 2782–3003), a ColE 1 origin of DNA replication (bp 4992–5666) and an ampicillin resistance coding region (bp 3987–4847).

In a method of the present invention, infectious, replication-defective EIAV particles may be prepared according to the methods disclosed herein in combination with techniques known to those skilled in the art. The method includes transfecting an lentivirus-permissive cell with the vector expression system of the present invention; producing the EIAV-derived particles in the transfected cell; and collecting the virus particles from the cell. The step of transfecting the lentivirus-permissive cell can be carried out according to any suitable means known to those skilled in the art. For example, in a method of the present invention, the three-plasmid expression system described herein is used to generate EIAV-derived retroviral vector particles by transient transfection. As another example, uptake of the vectors into the cells can be achieved by any suitable means, such as for example, by treating the cells with DEAE-dextran, treating the RNA with "LIPOFECTIN®" before addition to the cells, or by electroporation. These techniques are well known in the art.

The step of facilitating the production of the infectious viral particles in the cells may also be carried out using conventional techniques, such as by standard cell culture growth techniques.

The step of collecting the infectious virus particles may also be carried out using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

If desired by the skilled artisan, lentiviral stock solutions may be prepared using the vectors and methods of the present invention. Methods of preparing viral stock solutions are known in the art and are illustrated by, e.g., Y. Soneoka et al., *Nucl. Acids Res.* 23, 628–633 (1995) and N. R. Landau et al., *J Virol.* 66, 5110–5113 (1992). In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The vectors of the present invention are also useful in preparing stable packaging cells (i.e. cells that stably express EIAV virus proteins, which cells, by themselves, cannot generate infectious virus particles). Methods for preparing packaging cells that express retrovirus proteins are known in the art and are exemplified by the methods set forth in, for example, U.S. Pat. No. 4,650,764 to Temin et al., which disclosure is incorporated herein in its entirety. Within the scope of the present invention, a packaging cell will comprise a lentivirus-permissive host cell comprising an EIAV nucleic acid sequence coding for at least one EIAV structural protein, which nucleic acid sequence is packaging-signal defective, thus rendering the cell itself capable of producing at least one EIAV structural protein, but not capable of producing replicotion-competent infectious virus. In one embodiment, the EIAV nucleic acid sequence is an EIAV gag-pol expression vector such as, for example, pEV53. A packaging cell may be made by transfecting an EIAV-permissive host cell (e.g., a human embryonic kidney 293 cell) with a suitable EIAV nucleic acid sequence as provided above according to known procedures. The resulting packaging cell is thus able to express and produce at least one EIAV structural protein. However, in that the EIAV nucleic acid sequence is defective in the packaging signal, the cell, on its own, is not able to produce replication-competent EIAV virus. The packaging cell may then be transfected with other nucleic acid sequences (e.g., pEC-puro, pEC-lacK or pCI-VSV-G), which may contain heterologous genes of interest and an appropriate packaging signal. Once transfected with the additional sequence or sequences, the packaging cell may thus be used to provide stocks of EIAV viruses that contain heterologous genes, but which viruses are themselves replication-incompetent.

Pharmaceutical formulations, such as vaccines, of the present invention comprise an immunogenic amount of the infectious, replication defective virus particles as disclosed herein in combination with a pharmaceutically acceptable carrier. An "immunogenic amount" is an amount of the infectious virus particles which is sufficient to evoke an immune response in the subject to which the pharmaceutical formulation is administered. An amount of from about $10^3$ to about $10^7$ virus particles, and preferably about $10^4$ to $10^6$ virus particles per dose is believed suitable, depending upon the age and species of the subject being treated, and the immunogen against which the immune response is desired. Exemplary pharmaceutically acceptable carriers include, but are not limited to, sterile pyrogen-free water and sterile pyrogen-free physiological saline solution. Subjects which may be administered immunogenic amounts of the infectious, replication-defective virus particles of the present invention include but are not limited to human and animal (e.g., pig, cattle, dog, horse, donkey, mouse, hamster, monkeys) subjects.

Pharmaceutical formulations of the present invention include those suitable for parenteral (e.g., subcutaneous, intradermal, intramuscular, intravenous and intraarticular), oral or inhalation administration, Alternatively, pharmaceutical formulations of the present invention may be suitable for administration to the mucus membranes of a subject (e.g., intranasal administration). The formulations may be conveniently prepared in unit dosage form and may be prepared by any of the methods well known in the art.

The vectors and methods of the present invention are useful in in vitro expression systems, wherein the inserted heterologous genes located on the second vector encode proteins or peptides which are desirably produced in vitro.

The vectors, methods and pharmaceutical formulations of the present invention are additionally useful in a method of administering a protein or peptide to a subject in need of the desired protein or peptide, as a method of treatment or otherwise. In this embodiment of the invention, the heterologous gene located on the second vector of the present invention encodes the desired protein or peptide, and helper cells or pharmaceutical formulations containing the helper cells of the present invention are administered to a subject in need of the desired protein or peptide. In this manner, the protein or peptide may thus; be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

III. Gene Transfer Technology

The gene transfer technology of the present invention has several applications. The most immediate applications are perhaps in elucidating the process of peptides and functional domains of proteins. Cloned cDNA or genomic sequences for proteins can be introduced into different cell types in culture, or in vivo, in order to study cell-specific differences in processing and cellular fate. By placing the coding sequences under the control of a strong promoter, a substantial amount of the desired protein can be made. Furthermore, the specific residues involved in protein processing, intracellular sorting, or biological activity can be determined by mutational change in discrete residues of the coding sequences.

Gene transfer technology of the present invention can also be applied to provide a means to control expression of a protein and to assess its capacity to modulate cellular events. Some functions of proteins, such as their role in differentiation, may be studied in tissue culture, whereas others will require reintroduction into in vivo systems at different times in development in order to monitor changes in relevant properties.

Gene transfer provides a means to study the nucleic acid sequences and cellular factors which regulate expression of specific genes. One approach to such a study would be to fuse the regulatory elements to be studied to reported genes and subsequently assaying the expression of the reporter gene.

Gene transfer also possesses substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance which causes the disease or makes it more severe. The use of site-specific integration of nucleic sequences to cause mutations or to correct defects is also possible.

Hematopoietic stem cells, lymphocytes, vascular endothelial cells, respiratory epithelial cells, keratinocytes, skeletal and muscle cardiac cells, neurons and cancer cells are among proposed targets for therapeutic gene transfer, either ex vivo or in vivo. See, e.g., A. D. Miller, *Nature* 357, 455–460 (1992); R. C. Mulligan, *Science* 260, 926–932 (1993). These cells and others are suitable target cells for the vectors and methods of the present invention.

In summary, the viral vectors of the present invention can be used to stably transfect either dividing or non-dividing cells, and stably express a heterologous gene. Using this vector system, it is now possible to introduce into dividing or non-dividing cells, genes which encode proteins that can affect the physiology of the cells. The vectors of the present invention can thus be useful in gene therapy for disease states, or for experimental modification of cell physiology.

Having now described the invention, the same will be illustrated with reference to certain examples which are included herein for the purposes of illustration only, and which are not intended to be limiting of the invention.

EXAMPLE 1

Plasmid Construction

The parent plasmid for EIAV vectors described herein is the plasmid pER2. 1, generously provided by Dr. Fred Fuller of North Carolina State University, Raleigh, N.C., USA. The construction of the clone pER2.1 is described in S. T. Perry et al., *J. Virol.* 66, 4085–4097 (1992). pER2.1 encodes an infectious DNA clone of the Malmquist Wyoming strain of EIAV. One safety aspect of this clone is that the virus generated does not cause disease in its natural equine host. Also, unlike vectors derived from other retroviruses (e.g., murine leukemia virus, human immunodeficiency virus) considered for use in gene transfer, wild type EIAV does not mount an active infection in human cells.

EIAV gag/pol (first) expression vector. The pEV53 plasmid (shown in FIG. 2A) was designed to express EIAV proteins required for assembly and release of viral particles form cells, and includes genes encoding proteins encoded by the gag and pol genes, and the accessory proteins rev and tat. The open reading frame S2, encoding a protein whose function is not known, was also included. pEV53 was constructed to contain mutations that exclude retroviral-mediated transfer of viral genes. The mutations include sequence deletions in the viral env gene (thus excluding the possibility of generating replication-competent EIAV virus particles) and deletion of certain cis-acting sequence elements at the 3' end of the genome required for viral reverse transcription and integration. Deletions are included such that in the unlikely event that viral genes; are packaged into the infectious particles, they will not be replicated (e.g., replication-competent wild-type vectors will not be generated). The plasmid pEV53A, shown in FIG. 2B, is derived from pEV53, but differs from pEV53 in that all EIAV long terminal repeat (LTR) sequences containing promoter/enhancer elements and cis-acting sequence elements important for integration, as well as the tRNA primer binding site sequence for initiation of reverse transcription, have been deleted by removing nucleotides 902 through 1077 from pEV53). The pEV53A plasmid was made to further reduce the chances of retroviral-mediated transfer of viral genes without affecting the expression levels of EIAV proteins Gene Transfer (second) vector. The pEC-lacZ (shown in FIG. 3) and pEC-puro (shown in FIG. 4) plasmids were designed to serve as the vector for gene transfer and contain all cis-acting sequence elements required to support reverse transcription (e.g., replication) of the vector genome, as well as a multiple cloning site for insertion of cDNAs encoding genes of interest. The pEC-lacZ plasmid encodes the beta-galactosidase reporter gene lacZ, while the pEC-puro plasmid encodes the puromycin-N-acetyl transferase dominant selectable marker gene puro.

Viral envelope gene expression (third) vector. The third plasmid of the expression system described herein is the plasmid pCI-VSV-G, shown in FIG. 5. This plasmid expresses a viral envelope gene, specifically the vesicular stomatitis virus G glycoprotein gene.

EXAMPLE 2

Production and Testing of Viral Vectors

EIAV vectors were produced following standard calcium phosphate-mediated co-transfection of the pEV53 A gag-pol expression plasmid, the pCI-VSV-G env expression plasmid, and either the pEC-lacZ or pEC-puro expression vector plasmids into cultures of human 293 cells (American Type Culture Collection, Rockville, Md.). 48 hours after transfection, the culture medium was harvested from the cells and tested for EIAV vector production. The gene transfer efficiency of the pEC-puro vector was measured by the ability of serial dilutions of the vector to confer resistance to the drug puromycin. In this assay, an infected cell gives rise to a drug-resistant colony of cells, which can then be counted. Human 293 cells were used as the target cells. From six independent experiments, the average titer of the EC-puro vector was determined to be $2\pm1\times10^5$ colony forming units (cfu) per mL.

The gene transfer efficiency of the EC-lacZ vector was determined by staining infected human CFT1 human airway epithelial cells with X-gal (Molecular Probes, Inc., Eugene, Oregon), an analog of galactose. In this assay, cells expressing the beta-galactosidase gene will turn blue, and the percentage of blue cells is determined by counting. The titer of virus by multiplying the fraction of stained cells by the number of cells initially infected. In this manner, the titer of the EC-lacZ virus was determined to be about $5\pm1\times10^4$ infectious units (n=5) per mL.

Several control experiments were performed to determine whether the expression of the puro and lacZ genes were indeed mediated by viral components. In the first experiment, it was shown for both the EC-puro and EC-lacZ vectors that both the pEV53 or pEV53A and the pCI-VSV-G vectors were essential for gene transfer. The result is consistent with gene transfer and expression mediated by virus (and not free DNA). In a second control experiment using the lacZ vector, cells were stained with X-gal immediately after a two-hour infection and no blue cells were found. The result is consistent with temporal aspects of reverse transcription, integration and gene expression, which for other retroviruses are known to require a minimum of about 10 hours to complete.

EXAMPLE 3

Gene Transfer to Non-Dividing Cells

EIAV is capable of infecting non-dividing, terminally differentiated cells, such macrophages and airway epithelia. To test this property with the present invention, human CFT1 airway epithelial cells (generously provided by J. R. Yankaskas of the University of North Carolina at Chapel Hill) were arrested in the cell cycle with aphidicolin (Calbiochem-Novabiochem Corp., La Jolla, Calif.), and then infected with the pEC-lacZ vector. As a control, cells were infected in parallel with the LZ vector, a lacZ-containing retrovirus vector derived from the murine leukemia virus (MuLV). 48 hours after infection, cultures were stained for beta-galactosidase activity with X-gal. In the aphidicolin treated cultures, aphidicolin was present both during and after infection.

Figure 8:
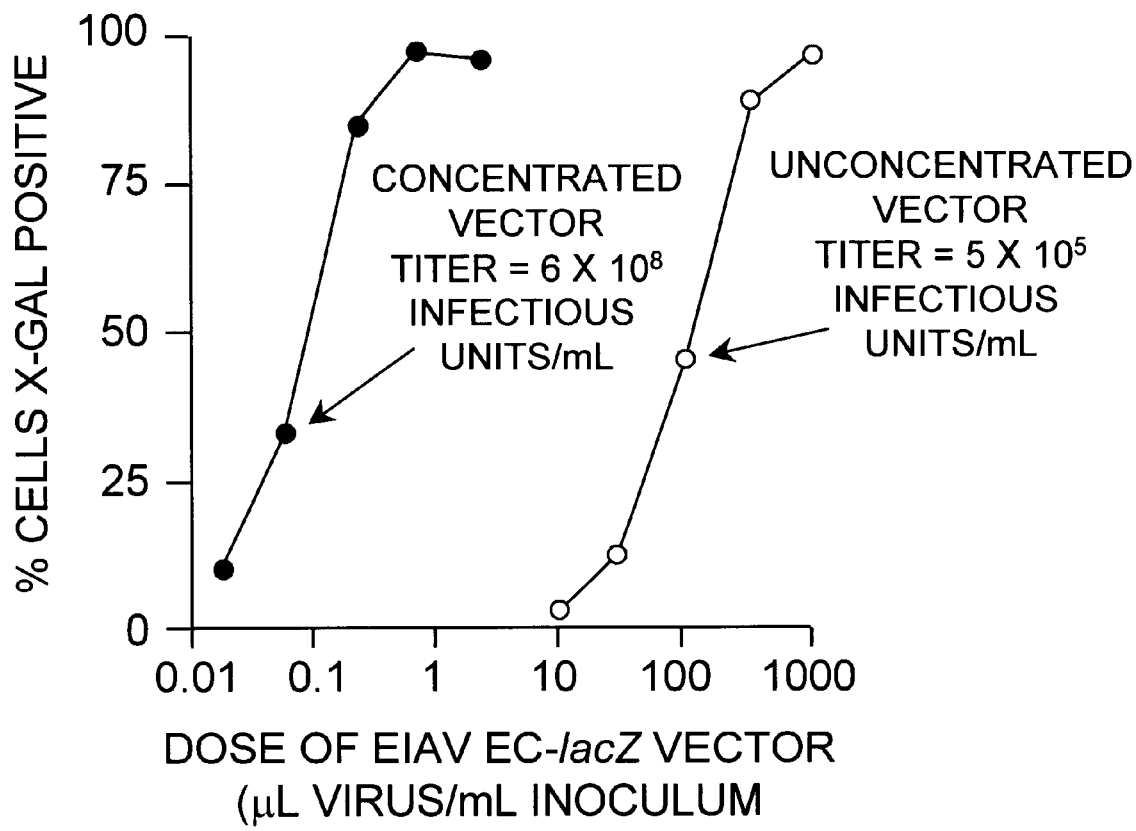
FIG. 8 is a dose-response curve of the infectivity of either unconcentrated (uncentrifuged) or concentrated (centrifuged) EC-lacZ/VSV-G pseudotyped virus particles.

Microscopic fields of the stained cells are shown in FIG. 8A. The LZ vector efficiently infected cells not treated with aphidicolin (upper left panel). However, when cells were arrested in the cell cycle by aphidicolin treatment, gene transfer efficiency dropped markedly (upper right panel). It was estimated by counting the rare blue-stained cell that the relative efficiency of gene transfer to dividing cells to non-dividing cells was about 100 to 1 for the LZ vector (as shown in FIG. 6B, left-hand pair of bar graphs). The results are consistent with results obtained in experiments in other laboratories. See e.g., D. G. Miller et al., *Mol. Cell. Biol.* 10, 4329–4242 (1990); P. F. Lewis and M. Emerian, *J. Virol.*, 68, 510–516 (1994). At the time of infection, parallel cultures were pulsed with bromodeoxyuridine (BrdU) for 2 hours to test the efficacy of the aphidicolin block and analyzed for BrdU incorporation into DNA, as shown in FIG. 6C. It was found that aphidicolin markedly reduced the incorporation of BrdU into DNA.

Figure 6A:
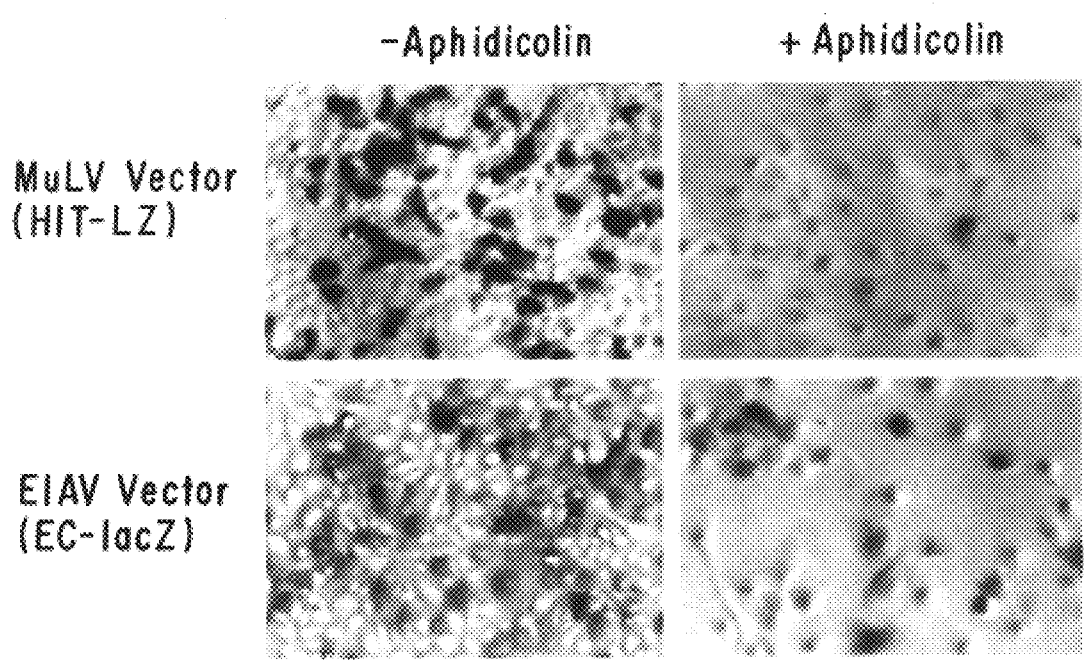
FIG. 6A contains four photographs illustrating gene transfer to dividing (left column) and non-dividing (right-column) cells by MuLV (top row) and EIAV vectors (bottom row), as described in Example 3, below.
Figure 6B:
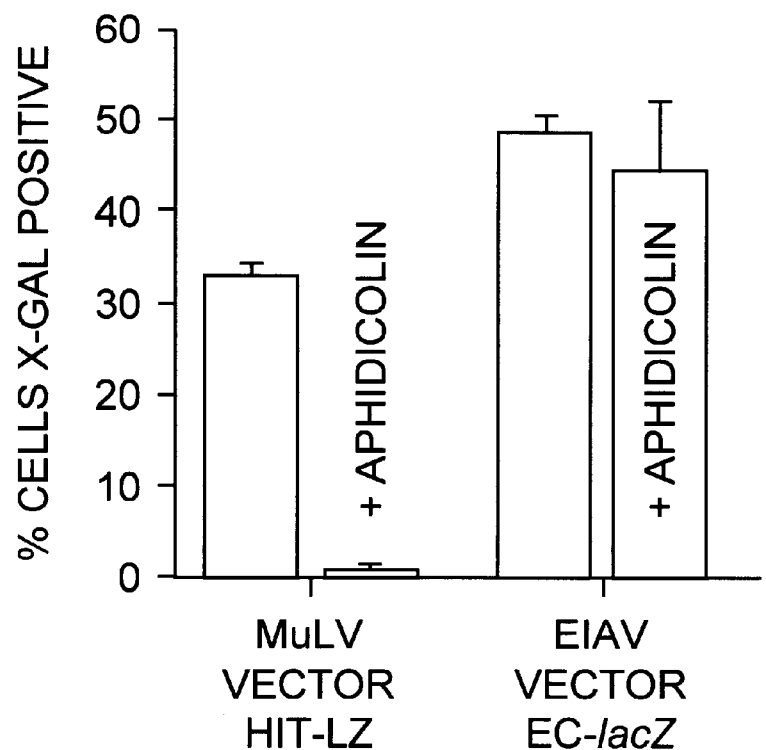
FIG. 6B is a graphical representation of the comparative efficiency of gene transfer to dividing and non-dividing cells by MuLV-based vectors (left-hand pair of bar graphs) and EIAV-based vectors (right-hand pair of bar graphs). Successful gene transfer is represented on the y-axis of the graph as the percentage of infected cells that are stained blue (i.e., are X-gal positive), as described below.
Figure 6C:
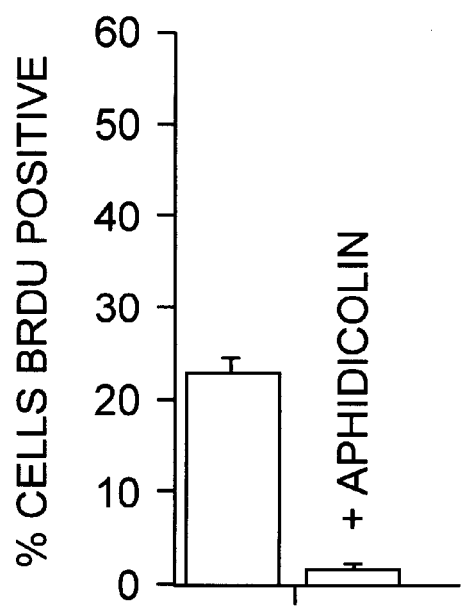
FIG. 6C is a graphical representation of the ability of aphidicolin to block the incorporation of bromodeoxyuridine (BrdU) into DNA in cells infected by MuLV-based gene transfer vectors. Successful gene transfer is represented on the y-axis of the graph as the percentage of infected cells that are positive for BrdU, as described in Example 3, below.
Figure 7:
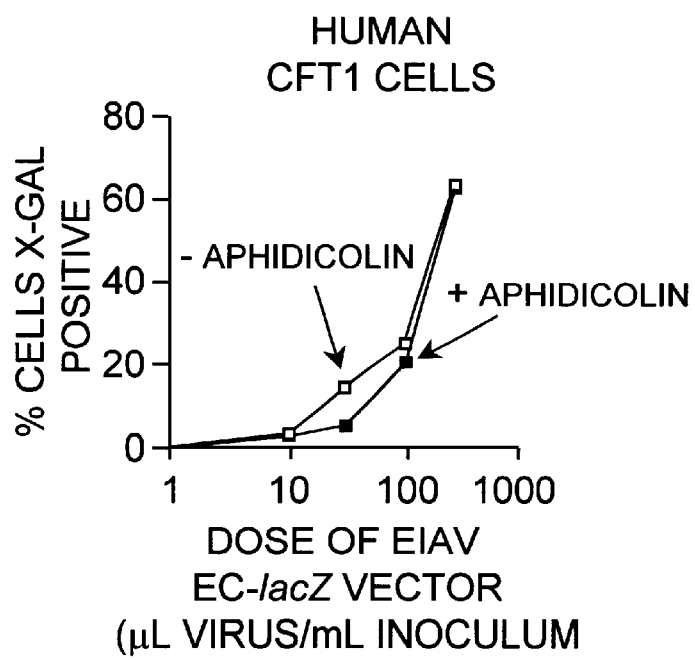
FIG. 7 contains two graphs illustrating the ability of the EIAV-based vector EC-lacZ to infect and transfer genes dividing and non-dividing cells. In the left-hand graph of FIG. 7, open circles represent human CFT1 cells not treated with aphidicolin, while closed circles represent human CFT1 cells treated with aphidicolin. In the right-hand graph of FIG. 7, open triangles represent equine dermal cells not treated with aphidicolin, while closed triangles represent equine dermal cells treated with aphidicolin. In both graphs, gene transfer is represented on the y-axis as the percentage of infected cells that are X-gal positive. In both graphs, dosage of the EC-lacZ vector is represented on the x-axis in units of $\mu$L virus/mL inoculum.
Figure 7:
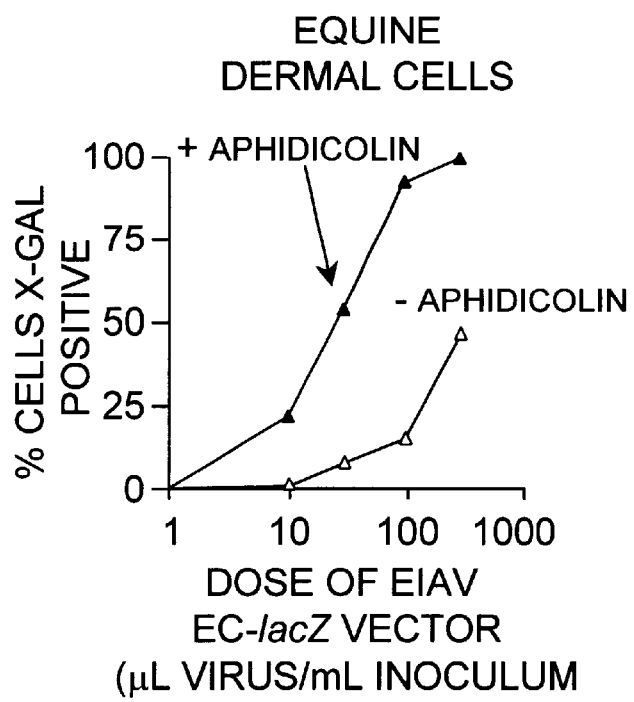

In contrast to the results obtained with the LZ vector, aphidicolin treatment had no significant effect on the percentage of human CFT1 cells infected by the EC-lacZ vector (see results in FIGS. 6A, lower panels, and 6B, right-hand pair of bar graphs). These results indicate that EIAV vectors can efficiently infect nondividing cells. For example, in the experiment shown in FIG. 7, the equine dermal fibroblast cell line NBL-6 was infected about 10 times more readily (for a given amount of virus), when cells were treated with aphidicolin, as compared to cells that were not treated with aphidicolin.

EXAMPLE 4

Ultracentrifugation of VSV-G Pseudotined EIAV Vectors

One advantage of VSV-G pseudotyped vectors is that the increased stability afforded by VSV-G permits concentration of infectivity by pelleting in an ultracentrifuge (see, e.g., J. C. Burns, et al., *Proc. Natl. Acac. Sci. USA* 90, 8033–8037 (1993)). It was determined that infectivity of VSV-G pseudotyped EIAV vectors can also be recovered by pelleting using centrifugation techniques. In this experiment, 720 ml of EC-lacZ-containing supernatant from a 2-plasmid (pEC-lacZ/pCI-VSV-G) co-transfection of 293 cells (stably modified to express the pEV53 plasmid) was concentrated by pelleting the virus in a high-speed centrifuge. The pellet was suspended in 0.36 ml of IX Hank's Balanced Salt Solution (HBSS, Cat.# 14175, Life Technologies, Inc., Gaithersburg, Md.) to achieve a 2000-fold concentration of virus particles. The infectivity was determined (see FIG. 8 for a dose-response curve of infectivity) and it was found that the titer increased about 1200-fold from $5\times105$ to $6\times10^8$. Thus, the yield of infectivity was about 60%. This result illustrates that EIAV vectors can be concentrated to high titers by pelleting.

EXAMPLE 5

Packaging Cell Line

For stable packaging cells, the human embryonic kidney cell line 293 was transfected using a standard calcium transfection procedure with pEV53. The cells were selected for expression of neomycin using G418 (geneticin) (Life Technologies Inc., Gaithersburg Md., USA). Individual colonies were selected, expanded and tested for virus production after transfecting with pECpuro and pCI-VSV-G. Clonal packaging cell lines showing the greatest vector production were either frozen for long-term storage or were maintained in culture for analysis of persistence of packaging function. It was found that the packaging function was stable for at least one month, indicating that the present invention is useful and successful in the preparation of stable, EIAV-based packaging cell lines.

While the invention has been described in connection with specific embodiments thereof, it will be understood that the invention is capable of further modification and this application is intended to cover any variations, uses or adaptations of invention following, in general, the principles of the invention and including such departures from the present disclosure as come within known or customary practice within the art to which the invention pertains, and as may be applied to the essential features set forth in the scope ofthe appended claims.

That which is claimed:

1. A recombinant lentiviral vector expression system comprising:
   (a) a first vector comprising an Equine Infectious Anemia Virus (EIAV) nucleic acid sequence encoding EIAV gag and EIAV pol, wherein said vector (i) comprises at least one defect in at least one gene encoding an EIAV structural protein, and (ii) comprises a defective packaging signal;
   (b) a second vector comprising an EIAV nucleic acid sequence comprising cis-acting sequence elements required for reverse transcription of the vector genome, wherein said vector (i) comprises a competent packaging signal, and (ii) comprises a multiple cloning site wherein a heterologous gene may be inserted; and
   (c) a third vector comprising a viral nucleic acid sequence, wherein said third vector (i) expresses a viral envelope protein, and (ii) comprises a defective packaging signal.

2. A vector system according to claim 1, wherein said second vector is deficient for expression of at least one EIAV structural protein.

3. A vector system according to claim 1, wherein said first vector, said second vector, and said third vector are obtained from cDNA clones of the EIAV genome.

4. A vector expression system according to claim 1, wherein said first vector is a gag-pol expression vector, and wherein said vector comprises a defect in the env gene.

5. A vector expression system according to claim 4, wherein said defect in the env gene is a deletion mutation.

6. A vector expression system according to claim 1, wherein said first vector and said second vector each comprise a defect in the env gene.

7. A vector expression system according to claim 1, wherein said third vector encodes an envelope protein that is not an EIAV envelope protein.

8. A vector expression system according to claim 1, wherein said third vector expresses the vesicular stomatitis virus G glycoprotein.

9. A vector expression system according to claim 1, wherein said second vector comprises a heterologous gene.

10. A vector expression system according to claim 9, wherein said heterologous gene encodes an antigenic protein or peptide.

11. A vector expression system according to claim 1, wherein said first vector is selected from the group consisting of the plasmid pEV53 and the plasmid pEV53A; said second vector is selected from the group consisting of pEC-lacZ and pEC-puro; and said third vector is the plasmid pCI-VSV-G.

12. The plasmid set forth in FIG. 2A as pEV53.
13. The plasmid set forth in FIG. 2B as pEV53A.
14. The plasmid set forth in FIG. 2 as pEC lacZ.
15. The plasmid set forth in FIG. 3 as pEC-puro.
16. The plasmid set forth in FIG. 4 as pCI-VSV-G.

17. A method of producing a replication-defective lentivirus particle, comprising transfecting a cell with:
   (a) a first vector comprising an Equine Infectious Anemia Virus (EIAV) nucleic acid sequence encoding EIAV gag and EIAV pol, wherein said vector (i) comprises at least one defect in at least one gene encoding an EIAV structural protein, and (ii) comprises a defective packaging signal;
   (b) a second vector comprising an EIAV nucleic acid sequence comprising cis-acting sequence elements required for reverse transcription of the vector genome wherein said vector (i) comprises a competent packaging signal, and (ii) comprises a multiple cloning site wherein a heterologous gene may be inserted; and
   (c) a third vector comprising a nucleic acid sequence of a virus, wherein said third vector (i) expresses a viral envelope protein, and (ii) comprises a defective packaging signal, wherein the cell produces a replication-defective lentivirus particle.

18. A method according to claim 17, wherein said cell is a non-dividing cell.

19. A method according to claim 17, wherein said second vector comprises a heterologous gene.

20. A replication-defective lentivirus particle produced according to the method of claim 17.

21. A cell comprising a replication-defective lentiviral particle, wherein said lentiviral particle is produced according to the method of claim 17.

22. An infectious EIAV particle comprising a nucleic acid sequence encoding a promoter and a gene sequence heterologous to EIAV, and wherein said nucleic acid sequence is defective in encoding at least one EIAV structural protein so that said virus particle is replication defective.

23. A method of producing a lentiviral stock comprising:
   (a) transfecting a lentivirus-permissive cell with
      (i) a first vector comprising an Equine Infectious Anemia Virus (EIAV) nucleic acid sequence encoding EIAV gag and EIAV pol, wherein said vector (1) comprises at least one defect in at least one gene encoding an EIAV structural protein, and (2) comprises a defective packaging signal;
      (ii) a second vector comprising an EIAV nucleic acid sequence comprising cis-acting sequence elements required for reverse transcription of the vector genome wherein said vector (1) comprises a competent packaging signal, (2) comprises a heterologous gene; and
      (iii) a third vector comprising a nucleic acid sequence of a virus, wherein said third vector (1) expresses a viral envelope protein, and (2) comprises a defective packaging signal;
   (b) growing the cell under cell culture conditions sufficient to allow production of replication-defective lentivirus particles in the cell; and
   (c) collecting said replication-defective lentivirus particles from the cell.

24. A method according to claim 23, wherein said producer cell is grown in a cell culture medium, and wherein said replication-defective lentivirus particles are collected from said medium.

25. A method of making a packaging cell, comprising transfecting a lentivirus-permissive cell with a vector comprising an EIAV nucleic acid sequence, wherein said vector comprises a defective packaging signal.

26. A method according to claim 25, wherein said vector is a gag-pol expression vector.

27. A method according to claim 25, wherein said vector is selected from the group consisting of the plasmid pEV53 and the plasmid pEV53 A.

28. A method according to claim 25, wherein said lentivirus-permissive cell is a human 293 cell.

29. A packaging cell comprising a lentivirus-permissive host cell comprising an EIAV nucleic acid sequence encoding at least one EIAV structural protein, wherein said nucleic acid sequence is packaging-signal defective, such that the cell itself produces at least one EIAV structural protein, but does not produce replication-competent infectious virus.

* * * * *